US006623312B2

(12) United States Patent
Merry et al.

(10) Patent No.: US 6,623,312 B2
(45) Date of Patent: Sep. 23, 2003

(54) PRECORDIAL ELECTROCARDIOGRAM ELECTRODE CONNECTOR

(75) Inventors: Rodney J. Merry, Woodinville, WA (US); Tom McGrath, Everett, WA (US); Paul O'Connor, Seattle, WA (US); Craig K. Black, Snohomish, WA (US); Matthew Pedersen, Seattle, WA (US); Robert J. Kelly, Camarillo, CA (US); William K. Wenger, Laguna Niguel, CA (US)

(73) Assignee: Unilead International, Lafayette, CA (US)

( * ) Notice: Subject to any disclaimer, the term of this patent is extended or adjusted under 35 U.S.C. 154(b) by 0 days.

(21) Appl. No.: 09/972,026

(22) Filed: Oct. 4, 2001

(65) Prior Publication Data
US 2003/0068914 A1 Apr. 10, 2003

(51) Int. Cl.$^7$ ................................................. H01R 4/48
(52) U.S. Cl. ......................... 439/729; 439/909; 439/91
(58) Field of Search ...................... 439/909, 86, 90–91, 439/729, 822, 491; 600/386, 391–393; 607/141, 152

(56) References Cited

U.S. PATENT DOCUMENTS

| 4,151,462 | A | * | 4/1979 | Teyler ........................ 324/72.5 |
| 4,353,372 | A | | 10/1982 | Ayer |
| 4,653,503 | A | | 3/1987 | Heath |
| 4,671,591 | A | | 6/1987 | Archer |
| 4,702,256 | A | | 10/1987 | Robinson et al. |
| 4,773,424 | A | | 9/1988 | Inoue et al. |
| 4,776,350 | A | | 10/1988 | Grossman et al. |
| 5,058,589 | A | | 10/1991 | Ding et al. |
| 5,176,543 | A | | 1/1993 | Brooks |
| 5,191,886 | A | | 3/1993 | Paeth et al. |
| 5,277,613 | A | * | 1/1994 | Neward ........................ 439/729 |
| 5,341,806 | A | | 8/1994 | Gadsby et al. |
| 5,355,883 | A | | 10/1994 | Ascher |
| 5,372,125 | A | | 12/1994 | Lyons |
| 5,405,273 | A | * | 4/1995 | Cartmell et al. ............. 439/822 |
| 5,582,180 | A | | 12/1996 | Manset et al. |
| 5,788,516 | A | * | 8/1998 | Uggmark ...................... 439/86 |
| 5,791,944 | A | | 8/1998 | Grant et al. |
| 5,797,771 | A | * | 8/1998 | Garside ........................ 439/610 |
| 5,895,369 | A | * | 4/1999 | Flower ........................ 604/20 |
| 5,967,817 | A | | 10/1999 | Greenstein |
| 6,048,218 | A | | 4/2000 | Greenstein |
| 6,062,915 | A | * | 5/2000 | Costello et al. ............. 439/729 |
| 6,152,754 | A | * | 11/2000 | Gerhardt et al. ............ 439/325 |
| 6,223,088 | B1 | * | 4/2001 | Scharnberg et al. ........ 607/142 |
| D452,318 | S | | 12/2001 | Merry et al. |
| 6,357,089 | B1 | * | 3/2002 | Koguchi ........................ 24/536 |

* cited by examiner

Primary Examiner—Tho D. Ta
Assistant Examiner—L. Tsukerman
(74) Attorney, Agent, or Firm—Ingrassia Fisher & Lorenz, P.C.

(57) ABSTRACT

The present invention is directed to an electrocardiogram electrode connector for connecting an electrode to an electrocardiogram device that solves the problems with the Prior Art noted above as well as providing numerous advantages. The connector of the present invention comprises a lower portion having an electrode end and an ECG end, and an upper portion pivotally connected to the lower portion. The upper portion likewise has an electrode end and an ECG end. The connector also comprises a spring between the lower portion and the upper portion to bias the electrode ends together to clamp about an electrode. Further, the connector comprises an electrical assembly having an elastomeric electrical connector to provide electrical continuity between the electrode and the ECG device when the electrode ends of the lower portion and the upper portion of the connector are biased together.

40 Claims, 6 Drawing Sheets

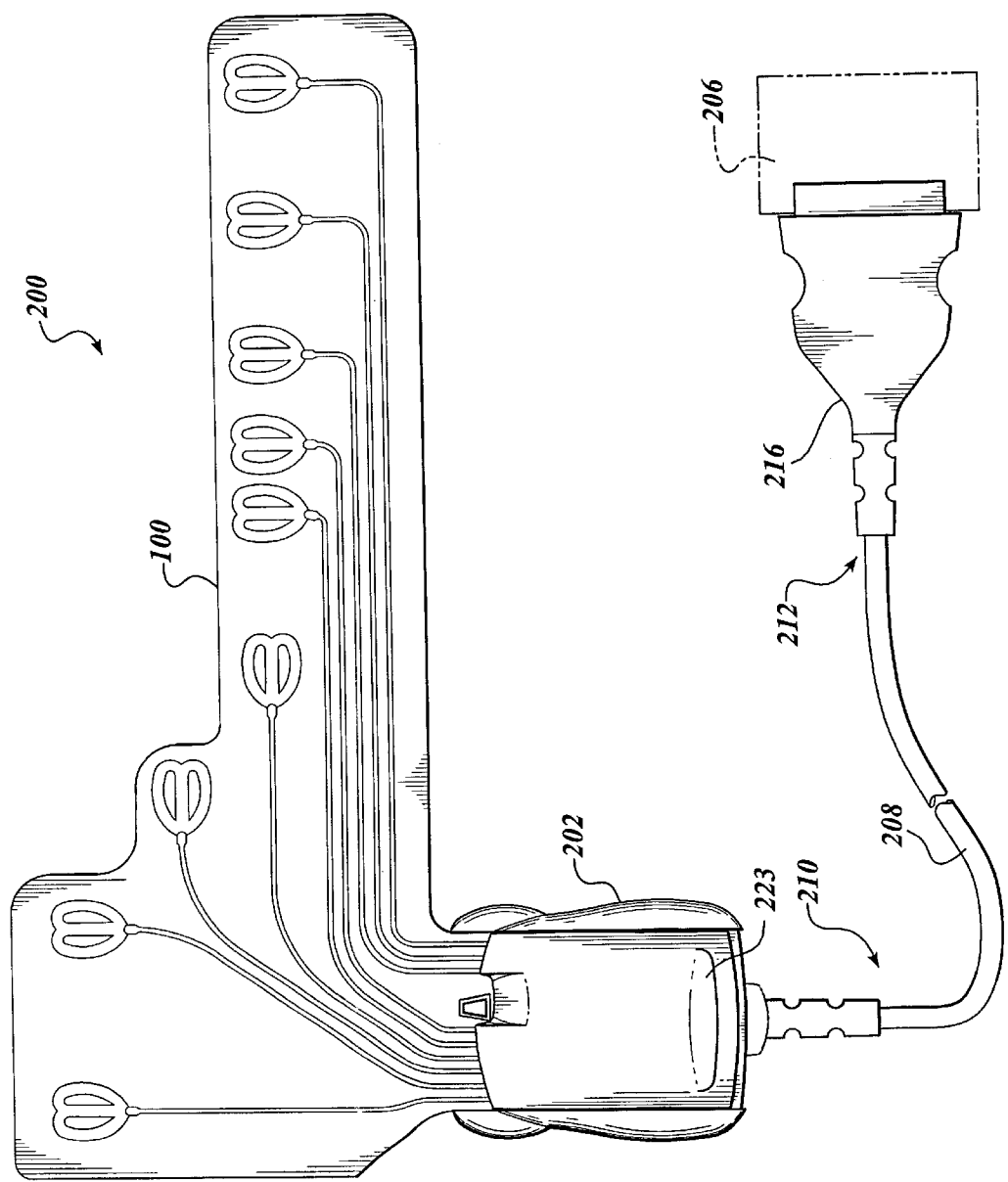

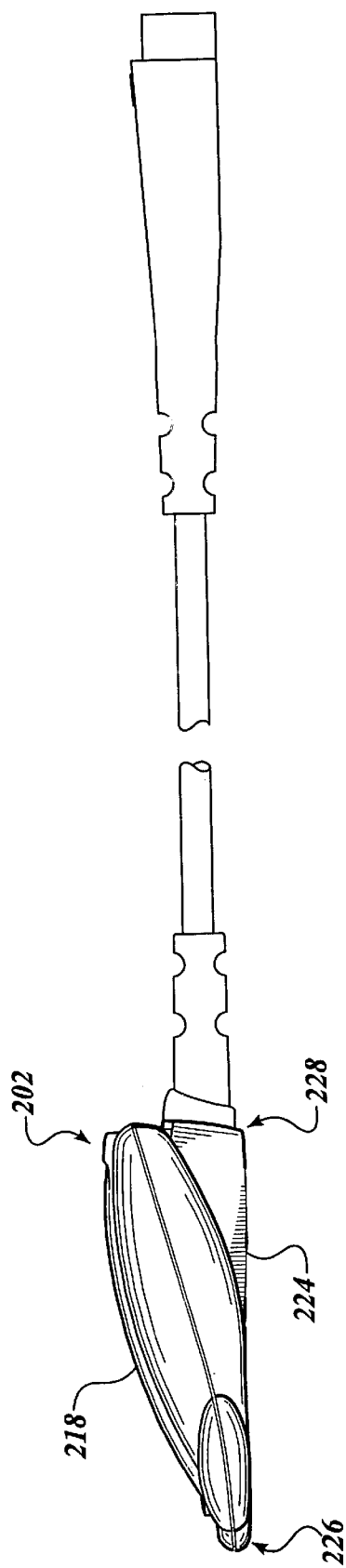

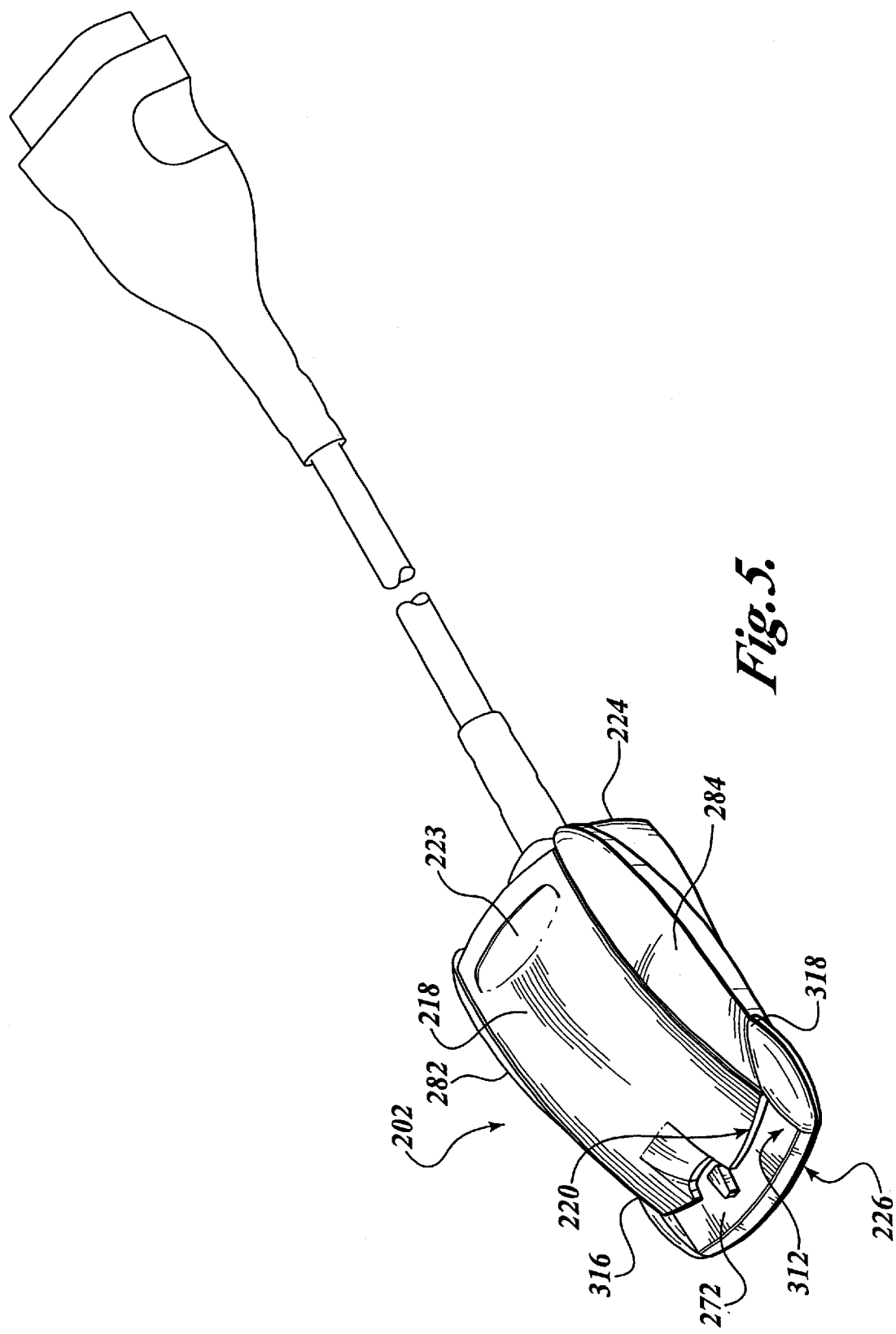

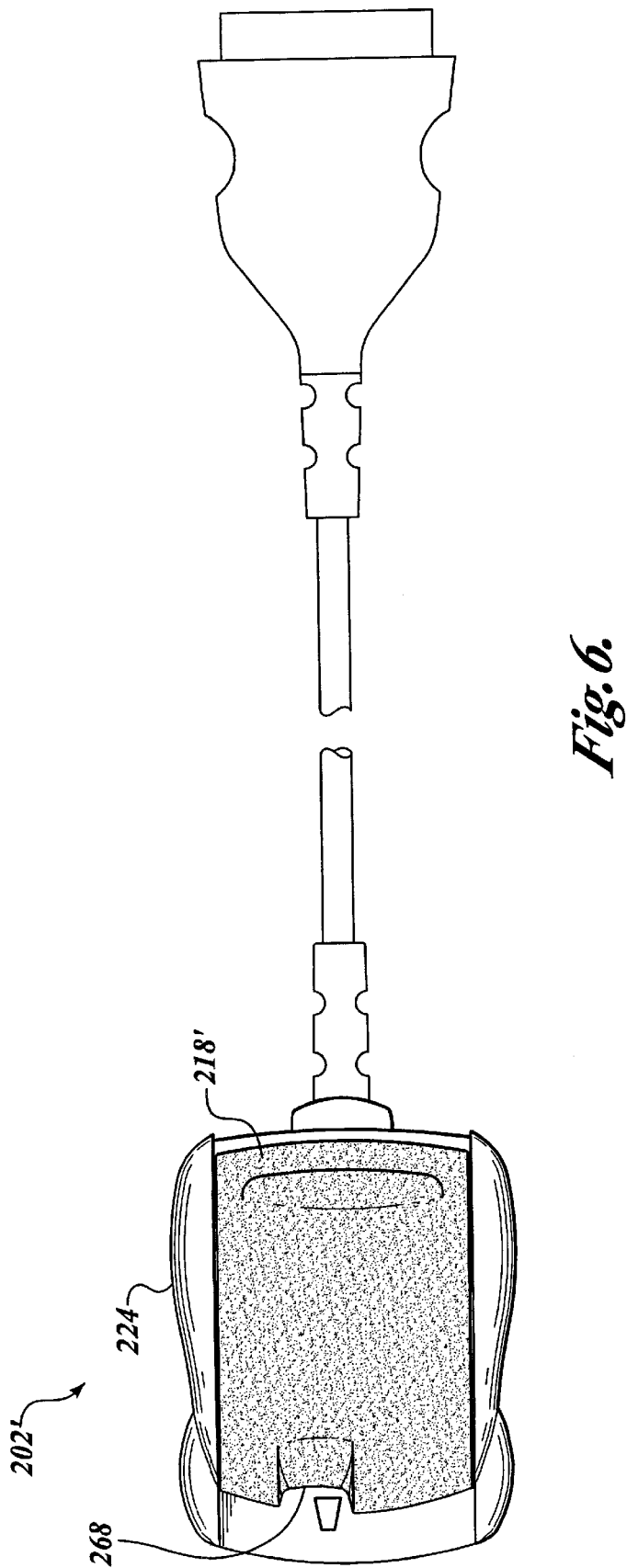

PRECORDIAL ELECTROCARDIOGRAM ELECTRODE CONNECTOR

FIELD OF THE INVENTION

The present invention relates to a precordial electrocardiogram (hereinafter "ECG") electrode connector used to connect an electrocardiogram electrode mask or sheet to a device capable of receiving ECG signals.

BACKGROUND OF THE INVENTION

Various electrocardiogram ("ECG") masks or sheets are well known in the art. Such sheets typically comprise a plurality of precordial electrodes fixed upon a flexible substrate that may be mounted upon a patient's chest for purposes of ECG monitoring. For example, U.S. Pat. No. 6,006,125 to Kelly et al. discloses a universal disposable ECG multiple sensor precordial electrode mask for monitoring ECG data from patients of differing sizes. A precordial electrode mask similar to that disclosed by Kelly et al. is illustrated in FIG. 1A (Prior Art). The mask includes a sheet material which carries up to nine electrodes on one side. One end of the electrode mask has sensors attachable to a patient and the other end has contacts attachable to a connector device. While the Prior Art discloses the use of some type of electrode connector or clip for connecting such a mask to an ECG device, the Prior Art is silent as to what an effective electrode connector would comprise.

In reality, an electrode mask is only one part of a complex and critical ECG medical system. Without the use of an effective connector, the electrode mask and the system are much less reliable. The problems with Prior Art electrode connectors are numerous. Previous connectors frequently incur misalignment problems between the connector contacts and the electrode contacts, previous connectors also tend to slip out of position when lying atop a person, and the previous connectors are easily dislodged from the electrode mask. In addition, the previous connectors are not easy to clean and lack ergonomic features, making them unreliable under certain circumstances.

SUMMARY OF THE INVENTION

The present invention is directed to an electrocardiogram electrode connector for connecting an electrode to an electrocardiogram device that solves the problems with the Prior Art noted above as well as providing numerous advantages. The connector of the present invention comprises a lower portion having an electrode end and an ECG end, and an upper portion pivotally connected to the lower portion. The upper portion likewise has an electrode end and an ECG end. The connector also comprises a spring between the lower portion and the upper portion to bias the electrode ends together to clamp about an electrode. Further, the connector comprises an electrical assembly having an elastomeric electrical connector to provide electrical continuity between the electrode and the ECG device when the electrode ends of the lower portion and the upper portion of the connector are biased together.

In an alternative embodiment of the present invention, an electrode connector is provided in which a locator pin is located on a surface of the base portion at the electrode end. The connector also includes an upper portion pivotally connected to the base portion, the upper portion likewise has an electrode end and an ECG end, wherein the upper portion electrode end includes an indentation capable of surrounding the locator pin on at least one side. The connector also includes a spring between the base portion and the upper portion to bias the electrode ends of the base portion and upper portion together, and an electrical assembly for providing electrical continuity between the precordial electrode and the ECG device.

In another embodiment of the present invention, the connector further comprises an elastomeric cover on a portion of the lower surface of the base portion. Raised side extensions are located on the base lower portion, so that the upper portion fits in between the first and the second side extensions. The connector spring is placed between the upper portion and the base portion and is suitably made as a leaf style spring. The base portion can be made from a first and a second base member where the upper base member contains the locator pin on a surface thereof. The connector is suitably made for connecting a precordial electrode to an ECG device. The connector further includes suitable grasping points formed on the base, and can have different colors for the base and the upper portion.

In yet another embodiment of the present invention, a precordial electrocardiogram electrode system is provided that comprises a precordial electrode mask, an ECG device, and an electrode connector as described above for connecting the electrode mask to the ECG device.

The electrode connector, constructed according to the present invention, provides a more reliable contact between the electrode mask and the ECG device by incorporating the elastomeric connector. The present electrode connector cures many of the problems due to misalignment. Further, the electrode connector's curved features make the connector ergonomic and simple to use. The two-tone color scheme also distinguishes the upper portion of the connector to indicate the differing parts and function, while an elastomeric covering on the connector's lower surface prevents the connector from slipping, and the indentation securely holds the electrode mask in place.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 2 shows a top plan view of a precordial electrocardiogram system, with a connector constructed according to the present invention connecting an electrode mask such as that shown in FIG. 1A to an ECG device;

FIG. 4 shows a side plan view of the connector constructed according to the present invention;

FIG. 5 shows a top perspective view of the connector constructed according to the present invention; and FIG. 6 shows a top plan view of an alternate embodiment of the connector constructed according to the present invention.

DETAILED DESCRIPTION OF THE PREFERRED EMBODIMENT

Figures 1A, 1B:
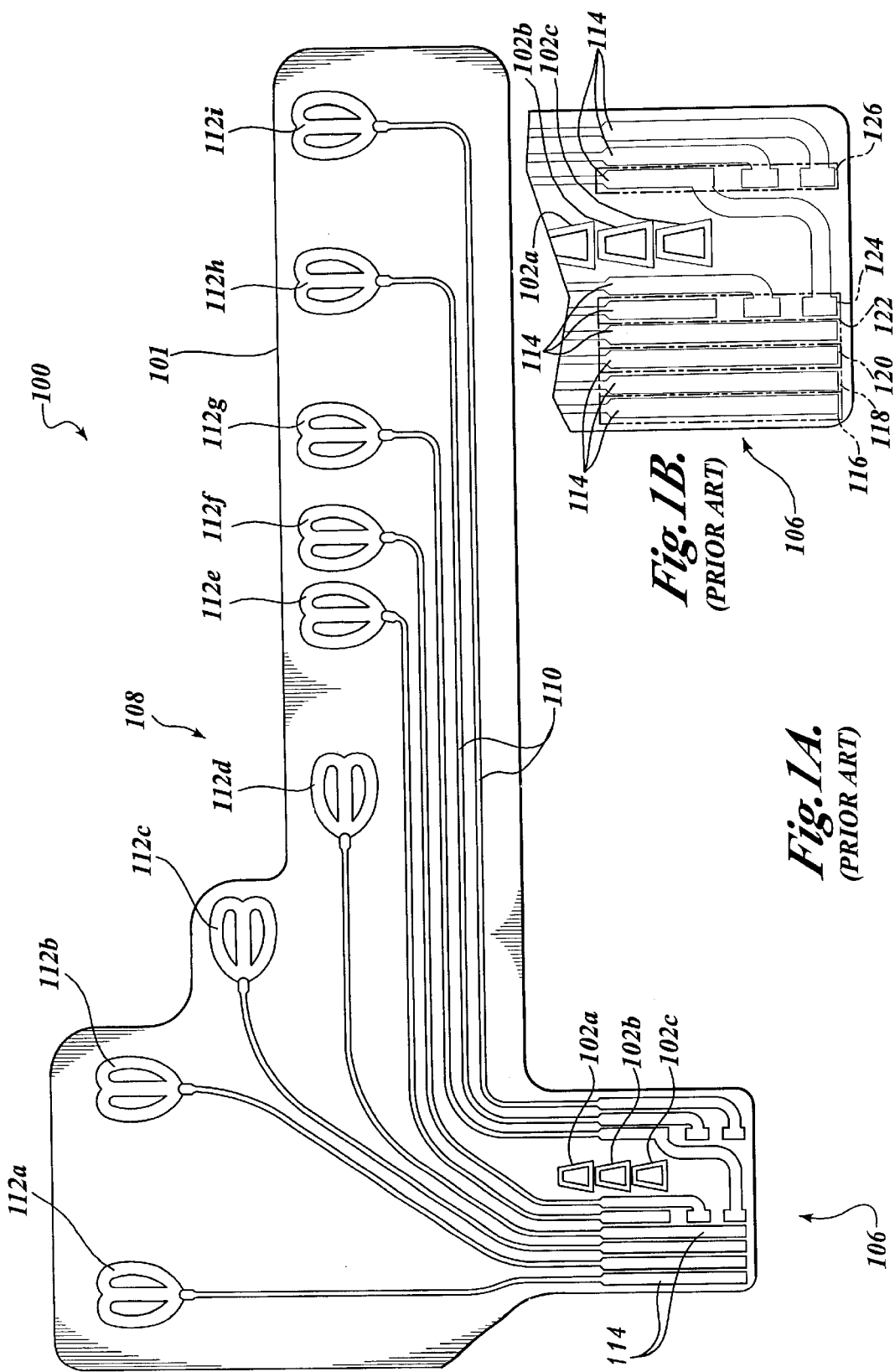
FIG. 1A (Prior Art) shows a top plan view of a Prior Art disposable precordial electrocardiogram electrode mask.
FIG. 1B (Prior Art) shows the connecting portion of the mask of FIG. 1A.

FIG. 2 shows a schematic illustration of a precordial electrocardiogram electrode system 200, formed in accordance with the present invention. The system 200 includes a disposable predodial electrode mask 100, which may be constructed similar to that shown in FIGS. 1A and 1B, an electrode connector 202, an electrocardiogram (ECG) device 206, and a cable 208 from the connector 20 to the EGG device 206. The cable 208 includes a connector end 210 and an EGG device end 12. The electrode mask 100 may be supplied by Medtronic Physio-Control Corp. of Redmond, Wash. In addition, a suitable electrode mask 100 is described in U.S. Pat. No. 6,006,125, the specification of which is herein incorporated by reference. The electrode mask 10 includes a translucent substrate sheet 101 to which sensors, leads and electrode contacts can e attached to one side thereof, forming the conducting side. The opposite side of the conducting side forms the non-conducting side. The electrode mask 100 also includes three locator cut outs 102a, 102b, 102c, and labeling indicia (not shown) used to size the mask 100 for small, medium and large torsos. The electrode mask 100 has a connecting portion 106 and a sensor portion 108. The electrode mask 100 includes a plurality of leads 110 terminating in electro e sensors 112 located in the sensor portion 108 and electrode contacts 114 locate in the connecting portion 106 of the electrode mask 100. The locator cut-outs 102a, 102b, and 102c are suitably shaped for engagement to an electrode connector, formed n accordance with the present invention, thus allowing the electrode mask 100 to be selectively engaged to the electrode connector 202 for connecting a selected one of the three sets of six sensors to the EGG device 206, depending on the torso size. As used herein, "electrode connector" designates a device for connecting the electrode mask 100 to an EGG device 206, such as an EGG monitor and/or defibrillator. Unless stated otherwise, "connector" will mean an "electrode connector."

The contacts 114 of the electrode mask 100 are arranged in a predetermined manner wherein one of three sets of six electrode sensors 112 can be in contact with an electrode connector for the three corresponding torso sizes. For example, referring to FIG. 1B (Prior Art), the connecting portion 106 can be considered to have six areas of contact 116, 118, 120, 122, 124, and 126. These distinct areas are defined to include a narrow strip of the contacting portion 106 having one or more electrode contacts 114 on the conducting side of the mask 100 and the non-conducting sheet 101 on the opposite side thereof, such that contact areas have both a conducting and non-conducting side. Contact areas 116, 118, 120, and 122 contain a single electrode contact 114 which substantially fills the contact area, respectively connected to sensors 112a, 112b, 112c and 112d. However, contact areas 124 and 126 each have three distinct electrode contacts 114. Contact area 124 has contacts for sensors 112e, 112f, and 112g, while contact area 126 has contacts for sensors 112g, 112h, and 112i. Sensor 112g as noted has contacts in two different contact areas 124 and 126. From FIG. 1B, it is apparent that the electrode contacts 114 of contact areas 124 and 126 are arranged in-line and separated by a gap of non-conducting material so as to electrically isolate the electrode contacts in contact areas 124 and 126. Also apparent from FIG. 1B is the arrangement of locator cut-outs 102 in an in-line fashion. The distances between cut-outs 102 correspond to the distances separating electrode contacts in areas 124 and 126. Therefore, when the connecting portion 106 is to be inserted in the connector 202 of the present invention, a locator pin 270 as will be described in more detail below is inserted into one of the three locator cut-outs 102, the amount of connecting portion 106 that is allowed to be inserted (i.e., depending on which cut-out 102a, 102b, or 102c is placed over the locator pin) determines which of the three sets of electrodes is activated (i.e., enabled to send ECG signals to the ECG device). The connector 202 makes contact with electrode contacts 114 in areas 116, 118, 120, and 122 regardless of pin placement, but only makes contact with one of the three electrode contacts 114 in each of areas 124 and 126 depending on the pin placement. By selecting cut-out 102a, the upper contacts in areas 124 and 126 are selected corresponding to a small size torso; by selecting cut-out 102b, the middle contacts in areas 124 and 126 are selected corresponding to a medium size torso selected; and by selecting cut-out 102c, the lower contacts in areas 124 and 126 are selected corresponding to a large size torso. Contacts in areas 116, 118, 120, and 122 are always to be selected regardless of cut-out selection.

In one actual embodiment of the present invention, the ECG device 206 to which the electrode mask 100 is connected is a defibrillator (not shown in detail) capable of monitoring ECG data as well as delivering a therapeutic shock. One such defibrillator, known as the LIFEPAK® 12 defibrillator, is manufactured and sold by Medtronic Physio-Control Corp. of Redmond, Wash., the assignee of the present application. However, other ECG devices capable of providing ECG monitoring without therapeutic delivery may also be used in the precordial ECG electrode system 200 without departing from the spirit and scope of the present invention. The electrode connector 202 is attached to the ECG device 206 via the cable 208 with a male/female assembly 216 on an end opposite the connector end 210.

Figure 3:
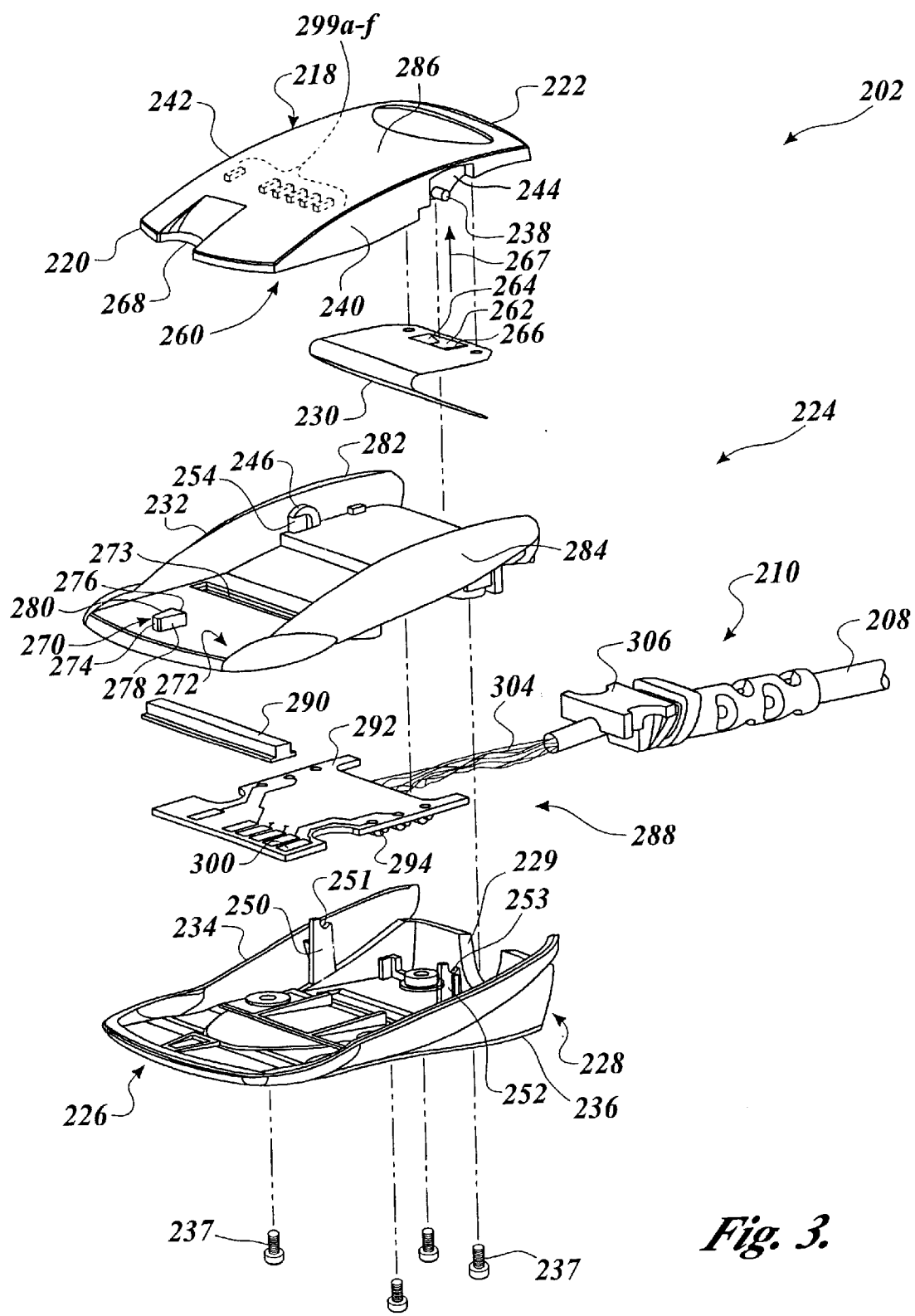
FIG. 3 shows an exploded view of the connector constructed according to the present invention.

Referring now to FIG. 3, an electrode connector 202 constructed according to the present invention is illustrated in more detail to show its individual and internal components. The electrode connector 202 includes an upper portion 218 having an electrode end 220 and an ECG end 222, a lower or base portion 224, likewise having an electrode end 226 and an ECG end 228, and a spring 230 between the upper 218 and base portions 224. As used herein, "electrode end" and "ECG end" are meant to denote the relative alignment positions of the system components of FIG. 2. Referring again to FIG. 3, the base portion 224 further includes upper 232 and lower 234 base members. Upper 232 and lower 234 members are held together with fasteners 237, such as screws, but other well-known fastening methods are also suitable without departing from the spirit and scope of the present invention. In one embodiment of the present invention, the lower member 234 further includes an elastomeric covering 236 on a lower surface portion thereof, such as a thin urethane cover, to resist sliding off a patient's body. The urethane cover can be applied by well-known injection molding methods so that the elastomeric covering 236 and the lower member 234 form an integral unit. In an alternate embodiment of the invention, the elastomeric covering 236 is detachably fastened to the lower member 234. In a typical application of the ECG device, such as when the ECG device is incorporated with a defibrillator, a patient will be lying prone and stripped of clothing from the chest region in order to place the electrode sensors 112 directly next to the patient's skin. An elastomeric covering 236 on the underside of the base portion 224 will prevent the connector from slipping against the skin. The electrode connector 202 of the present invention further includes an electrical assembly 288 mounted between the upper 232 and lower 234 base members to provide electrical continuity between the electrode mask 204 and the ECG device 206.

As also shown in FIG. 3, the upper portion 218 of the connector 202 includes an upper surface 286 contoured so as to resemble an arcuate shape. The upper portion 218 also includes first 240 and second 242 buttressing walls located along the longitudinal sides of the connector's upper portion 218. Buttressing walls 240, 242 are formed as downwardly extending sides from the upper portion top surface 286. Buttress walls 240, 242 are considered "sides" of upper portion 218. Buttressing walls 240, 242 include features to provide a suitable opening and closing arrangement between the connector's upper portion 218 and base 224 as will be described below. First and second buttress walls 240, 242 include pivotal axles 238 projecting outwardly or perpendicularly from the first 240 and second 242 buttress walls of the upper portion 218, but mounted within a recessed portion 244, wherein the recesses are formed on buttress walls 240 and 242 so that axles 238 minimally extend beyond the side surfaces of the upper portion 218. While only a single axle is shown in FIG. 3, it should be readily apparent that the opposite side is configured similarly. The pivotal axles 238 are located about one-third of the distance from the upper portion ECG end 222. However, the pivotal axles can be located at any position along the outer length of the upper portion sides 240 and 242, to provide a levering effect between the upper portion 218 and base portion 224 so as to provide an opening and closing motion of the upper and base portion ends 220, 226, respectively.

Alternatively, other configurations to provide an opening and closing effect are possible. For example, pivoting axles may be located on the base portion rather than on the upper portion. In that instance, the upper portion would include apertures, or otherwise, to receive base portion axles. Alternatively, axles can also be provided on the interior surfaces of buttress walls with corresponding apertures to receive the axles on the base portion. Other opening and closing configurations are also possible without departing from the spirit and scope of the present invention. These alternates also form a part of this disclosure.

Referring again to FIG. 3, the upper base member 232 of the base portion 224 includes a first 246 and second (not shown) flange with openings 254 for engaging each of the respective pivotal axles 238 of the upper portion 218 therein and thereby attaching the upper portion 218 of the connector 202 with the base portion 224. While only a single flange with opening combination is shown, it should be readily apparent that the opposite second flange and opening are configured similarly. The lower base member 234 includes first 250 and second 252 posts for supporting the pivotal axles 238 on grooves 251, 253, therein. The posts 250, 252 also provide securement against the axles 238 disengaging from the base portion 224 by blocking the openings 254 of the flanges 246 when the connector 202 is assembled.

Referring still to FIG. 3, a spring 230 is located between the upper portion 218 and the upper base member 232 to bias the ECG end 222 of the upper portion 218 upwards, thereby biasing the electrode end 220 downwards and towards the base portion upper member 232, about the axles 238. This spring 230 is suitably constructed from metal, and preferably is formed into a folded "leaf" style spring. However, it is readily apparent that other spring devices can be used, such as coils and/or elastomeric materials to bias the upper and base portions, respectively, towards each other to form a clamping device. The spring 230 is secured to a spring post (not shown) projecting downwardly from the lower surface 260 of the upper portion 218. The spring 230 has a cut-out portion 262. The cut-out portion 262 resembles an "H" shape, thus creating a flexible first and second flap 264, 266, which allows the spring 230 to be slid upward in the direction of arrow 267 onto the post but resists movement in the opposite direction, thusly securing the spring to the post.

As also shown in FIG. 3, the upper portion 218 of the connector 202 includes an indentation 268 located off-center of the longitudinal mid-axis of the upper portion electrode end 220. The indentation provides a partial "viewing window" to the electrode mask underneath when engaged with the connector 202. Correspondingly, a locator pin 270 protrudes from the upper surface 272 of the upper member 232 of the base portion 224. The locator pin 270 is sized to fit within the electrode locator cut-outs or "pin holes" 102 of the electrode mask 100 shown in more detail in FIGS. 1A and 1B. In one embodiment, the locator pin 270 has the shape of a polyhedron, having four sides, so as to match the shape of the locator cut-outs 102 of the electrode mask 100. The electrode end side 274 of the locator pin 270 is shorter in width than its opposite ECG end side 276. The first 278 and second 280 sides of the locator pin 270 slope from the ECG end 276 side to the electrode end side 274. However, those of ordinary skill in the art will recognize that the locator pin 270 may be of any size and shape suitable for mating with the cut-outs of the electrode mask 100. A portion of the locator pin ECG end side 276 extends into the indentation 268 of the upper portion 218 of the connector 202 when the connector is closed as shown in FIG. 2, such that the sides of indentation 268 surround the pin 270 partially on three sides thereof. Suitably, there is a gap between the locator pin 270 and the indentation 268 so the locator pin does not interfere with the closing of the electrode connector 202.

In use, when an electrode ask 100 as illustrated in FIG. 1A is inserted between the base portion 224 and the upper portion 218 of the connector such that the locator pin 270 is inserted into the locator cut-out 102, the sides of the indentation 268 hold the electrode mask 100 in place more securely than if no indentation were present. This is a result of the combination of the raised locator pin 270 extending into the indentation 268 while the sides of the indentation 268 press downward on the electrode mask 100. Accordingly, the downward pressure on the electrode mask 100 retains the locator pin 270 within the locator cut-out 102 as opposed to a configuration where no indentation is present in the upper portion of the connector and the locator pin does not ex end into the upper portion. The electrode mask 100 is thus prohibited from folding at the end of the upper portion electrode end, which would cause the electrode mask 100 to bend over and above the locator pin 270, thus allowing the electrode mask 100 to slide out. Further, this configuration prohibits undesirable lateral movement of the electrode mask 100. The locator pin 270 is sized to accommodate any of the locator cut-outs 102 therein. As described above with reference to FIGS. 1A and 1B, each locator cut-out 102 in the electrode mask 100 labeled with an indicator which shows the appropriate torso size that is suitable to be use when the locator pin 270 is located within any particular locator cut-out 102. The "sizing cut-out" then determines which of the electrode contacts 114, and thus, which of the nine sensors 112 will be active. For example, if a responder determines that a patient is of a size that warrants the use of a small electrode mask, the responder would place the electrode mask's connecting portion 106 at the appropriate locator cut-out 102 that corresponds to the size of the patient. By doing so, the appropriate electrode contacts 114 are lined up to receive and transmit ECG signals to the ECG device 206.

Returning to FIG. 3, and the description of connector 202, the upper member 232 of the base portion 224 includes a first 282 and second 284 side extension rising upwards on opposite sides thereof. In one embodiment of the present invention, the side extensions 282, 284 are integral with the base portion upper member 232 and include the flanges 246 described above. When the connector is in the closed position, the inner surfaces of side extensions 282, 284 lie adjacent and substantially parallel to first and second outer surfaces of wall buttresses 240, 242 of the connector's upper portion 218. Accordingly, when closed, the top surface 286 of the upper portion 218 is substantially flush with the base side extensions 282, 284.

An electrical assembly 288 is also shown in FIG. 3 forming a part of the electrode connector 202. The electrical assembly 288 is used to continue the electrical signals from the electrode mask 204 through the connector 202 and to the ECG device 206 as illustrated in the system of FIG. 2. The electrical assembly 288 includes an elastomeric electrical connector 290, and a printed circuit board 292 with electrical components 294 mounted on a lower surface thereof. The printed circuit board 292 includes a plurality of electrode contact pads 300 on the upper surface thereof. The electrical assembly 288 is connected to the cable 208 at the connector end 210 with a female electrical connector (not shown) mounted on the underside of the printed circuit board 292 while the cable 208 carries a male adapter (not shown) at the corresponding connector end 210. The cable 208 includes a collar 306 with a groove which fits into an opening 229 of the lower base member 234 at ECG end 228. The electrical components 294 on the printed circuit board 292 form part of the electrical circuit between mask 100 and the ECG device 206 and are included to provide protection against device overload, as well as electrical shock to the users of the ECG device 206 or associated equipment. Such circuitry is well known in the art and has been included in previous connectors as a safety measure.

Generally, during the operation of the present invention, the ECG signals travel from the electrode mask 100 through the connector 202 through the electrical components 294, thus forming an electrical circuit. Each of the six circuits that begins at the electrode contact areas 116, 118, 120, 122, 124, and 126 and that ends at the ECG device 206 is provided with a resistor 294 in the circuit. The resistors 294 are suitably rated to operate under normal loads; however, if a spike in the voltage is detected, the resistors 294 limit the amount of current that passes through the circuit to a safe level, thus preventing high loads from reaching the ECG device 206. The safe level has been determined by experience, experimentation, and with thought to the intended use of the connector. The resistors 294 are suitably rated for a resistance of 51 kilo $\Omega$; however, other sizes are suitable depending on the circumstances in which the electrode mask and the ECG device are being used. The circuits of the electrode connector 202 are also designed to protect their users. For example, if a patient were to experience cardiac arrest while the electrode mask is attached to the electrode connector, therapeutic shock delivery devices may be placed on the patient while the electrode mask is still connected. If the patient is shocked, the circuits are designed to limit the current passing through the electrode connector 202 in the manner just described, thus preventing an unacceptably high amount of current from reaching any person in contact with the electrode connector 202 or the ECG device 206.

Referring still to FIG. 3, the elastomer electrical connector 290 is mounted to the base upper member 232 of the base portion 218 so as to make contact with the electrical contacts 300 of the printed circuit board 292 lying underneath. More specifically, the elastomeric connector 290 project through a slot 273 in the surface 272 of the upper member 232. The underside of the connector's upper portion 218 contains six ribs 299a–f to press downward on the elastomeric connector 290, protruding through the upper member 232 of the base portion 224, at predetermined positions that correlate to the contact areas of the electrode mask 100 to provide a reliable and misalignment tolerant connection to the electrode mask 100 of FIG. 1A. The elastomeric connector 290 is supplied by numerous vendors, such as the Advanced Connector Technology Corp. of Camarillo, Calif. or the Fujipoly America Corp. of Kenilworth, N.J. The elastomeric connector 290 is sometimes sold under the trademark ZEBRA®. The elastomeric connector 290 includes alternating regions of conductive carbon-filled layers and non-conductive silicone layers. The advantage to having a flexible elastomeric connector is that an elastomeric connector can be deflected and squeezed in between regular as well as irregular contacting surfaces. A suitable elastomeric connector is the carbon elastomeric connector supplied by Fujipoly America Corp. The carbon model can have as little as 140 conductive layers per inch and as many as 500 conductive layers per inch. While elastomeric connectors are well known, their use in electrode connectors has not been disclosed.

Referring momentarily to FIG. 1B, when the connecting portion 106 of the electrode mask 100 is inserted into the connector's electrode end, the six ribs (not shown) line up with the six contact areas 116, 118, 120, 122, 124, and 126 on the non-conducting side thereof. Depending on the depth to which the connecting portion 106 is inserted, and thus which of the locator cut-outs 102 is selected, each of the six ribs will come to overlie the connecting portion 106 of the mask 100 at one of the electrode contacts 114 located in each of the six contact areas. The electrode contacts 114 in the four contact areas 116, 118, 120, and 122 are continuously lined up regardless of the cut-out 102 selected because the electrode contacts 114 extend the whole length in these contact areas. However, the electrode contacts 114 in areas 124 and 126 are selectively lined up according to cut-out 102 selected because these areas have distinct unconnected electrode contacts 114 throughout the length of the contact area.

Referring back to FIG. 3, the printed circuit board 292 lies adjacent to the elastomeric connector 290 when the connector 202 is closed to provide for electrical continuity between the elastomeric electrical connector 290 engaged with the electrode contacts 114 of the electrode mask 100 and the ECG device 206. The printed circuit board 292 includes contact pads 300, spatially located substantially corresponding to the ribs on the underside of the connector's upper portion 218 to make contact with the elastomeric electrical connector 290.

Referring now to FIGS. 1A and 2, as described above, the electrode mask 100 includes a plurality of contacts 114 which are placed in contact with the connector 202 of FIG. 3 via the elastomeric electrical connector 290 when the connector 202 is closed. Accordingly, depending on the size of the patient and thus, the selection of cut-out 102a, 102b, or 102c placed over the locator pin 270, six of the available sensors 112 are activated as described above, i.e., electrical signals from six of the sensors are conducted via the elastomeric electrical connector 290 to the electrical components 294 mounted on the printed circuit board 292 and ultimately to the ECG device 206 via the cable 208 as shown in FIG. 2. The female adapter (not shown) located on the printed circuit board 292 connects the printed circuit board 292 to the cable wires 304 attached to the connector end 210 of the cable 208. A further connector assembly 216, opposite the connector end 210 connects the connector 202 of the present invention to an ECG device 206 as shown in FIG. 2.

Referring now to FIG. 4, other particular features of the electrode connector according to the present invention are illustrated. The electrode connector 202 (or 202' of FIG. 6) of the present invention is contoured and colored to be simple to use in actual operation. From a side perspective view, the electrode connector 202 has a curved downward sloping outline imparted by side extensions on base member 224 and to the upper portion 218. The lower surface of the base 224 is generally flat. The profile of the electrode end 226 of the connector 202 is thus thinner than the profile of the connector ECG device end 228. The advantage of this construction is to enable a responder to grasp the appropriate connector ends and securely position the connector on the appropriate electrode mask 100 pin hole 102.

Referring now to FIG. 5, from a top perspective view, the upper portion of the electrode connector 202 (or 202') at the electrode end 220 terminates before the base portion 224 at the base electrode end 226 thus, forming a ledge region 312 from the base upper surface 272. An abrupt change in surface contours of the first and second side extensions 282 and 284 of the base portion 224 forms suitable grasping points 316 and 318 for the connector 202 (or 202'). The grasping points 316 and 318 are also bounded by outwardly projecting portions from the sides of the base portion 224. The combination of curvilinear features prompts the responder to grasp the connector 202 (or 202') in the most efficient and ergonomic manner. Further, the unique contours prevent the connector 202 (or 202') from accidentally slipping out of the responder's hand. In actual use, the connector 202 (or 202') can become covered in body fluids as in many instances when defibrillator is employed by emergency teams and, thus, suitable grasping points are included.

Referring collectively to FIGS. 1–5, the electrode connector 202 made according to the present invention is used in the following manner. An electrode mask 100 is provided. The electrode connector 202 is squeezed manually at the ECG ends 222, 228 of the base and upper portion so as to provide an opening at the electrode ends 220, 226 for insertion of the connecting portion 106 of the electrode mask 100 into the connector 220. A locator cut-out 102 is selected according to the patient's size (e.g., small, medium or large) and the locator pin 270 is located into the locator cut-out 102. The pressure on the ECG ends 222, 228 of the base 224 and the upper portion 218 is released to allow the electrode ends 220, 226 to close over and under the connecting portion 106 of the electrode mask 100. At this point, the indentation 268 located on the upper portion electrode end 220 partially surrounds the locator pin 270. The sides of the indentation 268 suitably overlap a portion of the locator pin 270 as seen from above in FIG. 5 (and FIG. 6). In this manner, the electrode mask 100 is held securely on the electrode connector 202 until the ECG ends 222, 228 of the base 224 and upper portion 218 are again squeezed to open the electrode ends 220, 226 and allow removal of the electrode mask 100 from the connector 202.

The electrical assembly 288 operates in the following manner. The ribs (not shown) on the underside 260 of the upper connector's portion 218 press on the non-conducting side of the contact areas 116, 118, 120, 122, 124 and 126 of the electrode mask 100, which in turn presses the electrode contacts 114 against the elastomeric electrical connector 290 of the connector 202, thus providing electrical continuity between the electrode mask 100 and the elastomeric connector 290. In turn, the elastomeric connector 290 is forcibly pushed against the printed circuit board pads 300, thus providing electrical continuity between the elastomeric connector 290 and the board 292. The board 292 connects to the cable 208 via a plurality of wires 304, eventually leading to the ECG device 206. The use of an elastomeric electrical connector 290 in the electrical assembly 288 provides for greater misalignment tolerance between the electrode contacts 114 and the connector 202 of the present invention.

Referring now to FIG. 6, an alternate embodiment of the connector 202' according to the present invention is illustrated. In this embodiment, the upper portion 218' of the connector 202' is of a different color than the base portion 224 assembly. This is to distinguish the moving upper portion 218' from the stationary base portion 224. In one actual embodiment, the upper portion 218' is colored a matte gray color, while the base portion 224 is a matte black color with a black urethane covering (shown in FIG. 3 as 236) on the lower surface portion of the base 224 to match the base color. A two-tone color scheme for the upper portion 218' and the base portion 224 provides for numerous advantages. For example, a responder can quickly recognize the two different squeezing locations which are necessary to be squeezed together in order to cause the opening of the electrode ends. The upper portion 218' includes a pigmentation of a different color than the base portion 224 so as to distinguish the upper portion 218' as the piece which is to be depressed.

While the preferred embodiment of the invention has been illustrated and described, it will be appreciated the various changes can be made therein without departing from the spirit and scope of the invention.

The embodiments of the invention in which an exclusive property or privilege is claimed are defined as follows:

1. An electrocardiogram (ECG) electrode connector for electrically connecting a plurality of electrode contacts on an electrode mask to an EGG device, comprising:

a lower portion having an electrode end, an EGG end, a top surface, and a lower surface; an upper portion pivotally connected to the lower portion, the upper portion having a top surface, a lower surface, an electrode end, and an EGG end;

a spring between the lower portion and the upper portion to bias the electrode ends together; and an electrical assembly comprising an elastomeric electrical connector; and a plurality of protrusions extending from the upper portion lower surface, each of the protrusions collocated with at least a portion of the elastomeric electrical connector and with at least one of the plurality of electrode contacts, wherein electrical continuity is provided between individual ones of the plurality of electrode contacts on the electrode mask and the EGG device when the electrode ends of the lower portion and the upper portion of the connector are biased together.

2. The connector of claim 1, further comprising an elastomeric covering on a portion of the lower surface of the lower portion.

3. The connector of claim 1, further comprising first and second raised side extensions located on the lower portion, wherein the upper portion fits in between the first and second side extensions.

4. The connector of claim 1, wherein the spring is a leaf style spring.

5. The connector of claim 1, wherein the electrode is a precordial electrode.

6. The connector of claim 1, further comprising a locator pin located on a surface of the connector, wherein the pin is suitably sized to accommodate sizing holes located on an electrode mask.

7. The connector of claim 1, further comprising an indentation located on a surface of the connector to suitably provide a viewing window to an electrode mask.

8. The connector of claim 1, further comprising grasping points bounded by projecting portions defined on the connector lower portion.

9. The connector of claim 1, wherein the lower portion is a different color than the upper portion.

10. The connector of claim 9, wherein the lower portion is black, and the upper portion is gray.

11. An electrocardiogram (ECG) electrode connector for electrically connecting a plurality of electrode contacts on an electrode mask to an EGG device, comprising:
   a base portion, the base portion having an electrode end, an EGG end, a top surface, and a lower surface wherein a locator pin is located on a surface of the base portion at the electrode end;
   an upper portion pivotally connected to the base portion, the upper portion having an electrode end and an EGG end, wherein the upper portion electrode end includes an indentation suitably sized to surround the locator pin on at least one side thereof
   a spring between the base portion and the upper portion to bias the electrode ends of the base portion and upper portion together;
   an electrical assembly to provide electrical continuity between the electrode contacts and the EGG device; and
   first and second sides extending upwardly from the base portion, wherein the upper portion at least partially fits in between the first and second raised sides.

12. The connector of claim 11, further comprising an elastomeric covering on a portion of the lower surface of the base.

13. The connector of claim 11, wherein the spring is a leaf spring.

14. The connector of claim 11, further comprising a first and second base member forming the base portion, wherein the upper base member includes the locator pin that is surrounded by the indentation.

15. The connector of claim 11, wherein the locator pin is suitably sized to accommodate sizing holes located on an electrode mask.

16. The connector of claim 11, wherein the electrical assembly further comprises an elastomeric electrical connector to provide electrical continuity between the electrode and the ECG device when the electrode ends of the base portion and the upper portion of the connector are biased together.

17. The connector of claim 11, wherein the electrode is a precordial electrode.

18. The connector of claim 11, further comprising grasping points bounded by projecting portions defined on the connector base portion.

19. The connector of claim 11, wherein the base portion is a different color than the upper portion.

20. The connector of claim 19, wherein the base portion is black, and the upper portion is gray.

21. An electrocardiogram (EGG) electrode system comprising:
   an electrode mask having a plurality of electrode contacts thereon;
   an EGG device for processing EGG signals sensed by the electrode mask; and
   an electrode connector for electrically connecting individual ones of plurality of electrode contacts to the EGG device, the electrode connector comprising:
      a base portion having an electrode end, an EGG end, a top surface, and a lower surface;
      an upper portion pivotally connected to the base portion, the upper portion having a top surface, a lower surface, an electrode end, and an EGG end;
      a spring between the base portion and the upper portion to bias the electrode ends of the base and upper portions together to clamp the electrode mask;
      an electrical assembly comprising an elastomeric electrical connector; and
      a plurality of protrusions extending from the upper portion lower surface, each of the protrusions collocated with at least a portion of the elastomeric connector and with at least one of the plurality of electrode contacts,
      wherein electrical continuity is provided between individual ones of the plurality of electrode contacts and the EGG device when the electrode ends of the lower portion and the upper portion of the connector are biased together.

22. The system of claim 21, wherein the electrode connector further comprises an elastomeric covering on a portion of the lower surface of the base portion.

23. The system of claim 21, wherein the electrode connector further comprises a first and second raised side extension located on the base portion, wherein the upper portion fits in between the first and second side extensions.

24. The system of claim 21, wherein the spring is a leaf style spring.

25. The system of claim 21, wherein the electrode mask is a precordial electrode mask.

26. The system of claim 21, wherein the electrode connector further comprises a locator pin located on a surface of the base portion, wherein the pin is suitably sized to accommodate sizing holes located on the electrode mask.

27. The system of claim 21, wherein the electrode connector further comprises an indentation located on a surface of the upper portion to suitably provide a viewing window to the electrode mask.

28. The system of claim 21, wherein the electrode connector further comprises grasping points bounded by projecting portions defined on the connector base portion.

29. The system of claim 21, wherein the base portion is a different color than the upper portion.

30. The system of claim 29, wherein the base portion is black and the upper portion is gray.

31. An electrocardiogram (EGG) electrode system, comprising:
   an electrode mask;
   an ECG device for processing EGG signals sensed by the electrode mask; and
   an electrode connector for connecting the electrode mask to the ECG device; the electrode connector comprising:
      a base portion, the base portion having an electrode end, an EGG end, a top surface, and a lower surface wherein a locator pin is located on a surface of the base portion at the electrode end;
      an upper portion pivotally connected to the base portion, the upper portion having an electrode end and an EGG end, wherein the upper portion electrode end includes an indentation suitably sized to surround the locator pin on at least one side thereof
      a spring between the base portion and the upper portion to bias the electrode ends of the base portion and upper portion together;
      an electrical assembly to provide electrical continuity between the electrode mask and the EGG device; and first and second sides extending upwardly from the base portion, wherein the upper portion at least partially fits in between the first and second raised sides.

32. The system of claim 31, wherein the electrode connector further comprises an elastomeric covering on a portion of the lower surface of the base portion.

33. The system of claim 31, wherein the spring is a leaf style spring.

34. The system of claim 31, wherein the electrode mask is a precordial electrode mask.

35. The system of claim 31, wherein the pin is suitably sized to accommodate sizing holes located on the electrode mask.

36. The system of claim 31, wherein the electrical assembly further comprises an elastomeric electrical connector portion, to provide electrical continuity between the electrode mask and the ECG device when the electrode ends of the base portion and the upper portion of the connector are biased together.

37. The system of claim 31, wherein the electrode connector further comprises grasping points bounded by projecting portions defined on the connector base portion.

38. The system of claim 31, wherein the base portion is a different color than the upper portion.

39. The system of claim 38, wherein the base portion is black and the upper portion is gray.

40. A method of using a bias-closed connector to connect an electrode mask to an ECG device, the method, comprising:

providing an electrode mask having a plurality of sizing holes;

selecting one of the sizing holes based upon a patient's size;

inserting a connecting portion of the mask in the electrode connector by manually opening the connector and fitting the selected sizing hole to a pin located on a surface of the connector; and closing the connector by releasing the ends so that the mask is held within the connector at least in part by the pin and an indentation formed on the connector.

* * * * *

UNITED STATES PATENT AND TRADEMARK OFFICE
CERTIFICATE OF CORRECTION

PATENT NO. : 6,623,312 B2
DATED : September 23, 2003
INVENTOR(S) : Rodney J. Merry et al.

It is certified that error appears in the above-identified patent and that said Letters Patent is hereby corrected as shown below:

Column 10,
Lines 32, 33, 37 and 50, delete "EGG" and add -- ECG --;

Column 11,
Lines 13, 15, 19 27, 59, 63 and 67, delete "EGG" and add -- ECG --;
Line 21, add -- ; -- after "thereof";

Column 12,
Lines 1, 5, 18, 47, 50, 55, 60 and 67, delete "EGG" and add -- ECG --;
Line 62, add -- ; -- after "thereof".

Signed and Sealed this

Twenty-third Day of December, 2003

JAMES E. ROGAN
*Director of the United States Patent and Trademark Office*